United States Patent
Kurono et al.

Patent Number: 5,434,165
Date of Patent: Jul. 18, 1995

[54] NOOTROPIC AGENTS, COMPOSITIONS OF, AND METHOD OF USE THEREOF

[75] Inventors: Masayasu Kurono; Yutaka Baba; Tomoo Suzuki; Tsunemasa Suzuki; Kiyotaka Hirooka; Kiichi Sawai, all of Aichi, Japan

[73] Assignee: Sanawa Kagaku Kenkyusho Company, Ltd., Nagoya, Japan

[21] Appl. No.: 976,499

[22] Filed: Nov. 13, 1992

[30] Foreign Application Priority Data

Nov. 18, 1991 [JP] Japan ................... 3-302070

[51] Int. Cl.⁶ .................. C07D 471/04; C07D 403/14; A61K 31/47; A61K 31/41
[52] U.S. Cl. ..................... 514/313; 514/312; 514/314; 514/400; 546/101; 546/108; 546/159; 546/162; 548/153
[58] Field of Search ............... 548/452; 546/162, 101, 546/108, 159; 514/312, 314, 413

*Primary Examiner*—David B. Springer
*Attorney, Agent, or Firm*—Sughrue, Mion, Zinn, Macpeak & Seas

[57] ABSTRACT

An aromatic amino-substituted compound represented by formula:

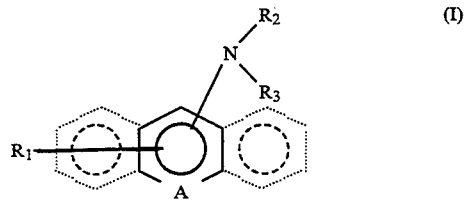

wherein A represents CH, N, or N→O; $R_1$ represents a nitro group or an amino group; $R_2$ represents a hydrogen atom, a lower alkyl group, or an acyl group; and $R_3$ represents a group:

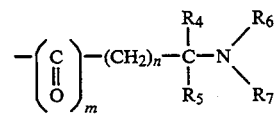

wherein $m$ represents 0 or 1; $n$ represents an integer of from 0 to 3; $R_4$ and $R_5$ each represents a hydrogen atom or a lower alkyl group; $R_6$ and $R_7$ each represents a hydrogen atom or a straight chain or branched lower alkyl group; $R_4$ and $R_6$ may be joined together to form an alkylene chain forming a heterocyclic ring; $R_5$ and $R_7$ may be joined together to form an alkylene chain forming a heterocyclic ring and $R_6$ and $R_7$ may be joined together to form an alkylene chain forming a heterocyclic ring, or a pharmaceutically acceptable salt thereof, a process for producing the same, and a method for preventing or treating brain disfunction such as senile dementia or Alzheimer's disease by administering a nootropic agent containing the same as an active ingredient are disclosed.

12 Claims, No Drawings

NOOTROPIC AGENTS, COMPOSITIONS OF, AND METHOD OF USE THEREOF

FIELD OF THE INVENTION

This invention relates to a novel compound or a salt thereof useful as a nootropic agent for the prevention and treatment of cerebral dysfunction and also relates to a process for preparing the same and to a method of preventing or treating cerebral dysfunction. More particularly, the present invention relates to a preventing and treating agent effective for senile dementia or Alzheimer's disease.

BACKGROUND OF THE INVENTION

In recent years, dementia, memory retention defect, aphasia, apraxia, psychosis, and Alzheimer's disease, increased by the large expansion of the elderly population, changes in the social environment, etc., have been an increasing social problem. In particular, the cause and therapy of Alzheimer's disease are still being investigated.

Although 1,2,3,4-tetrahydro-9-aminoacridine, abbreviated as THA, has recently been developed as a treating agent for Alzheimer's disease in the United States and has attracted attention, it has not yet obtained approval from the FDA (Food and Drug Administration). The reason for the disapproval appears to relate to the question of efficacy and adverse reactions of THA. Therefore, it has been keenly demanded to develop an antidementic agent having potent pharmacological effects and excellent safety. The development of THA has accelerated development of antidementics worldwide, but no drug having potent antidementic effect and excellent safety which relieves patients from dementia on the clinical stage has been developed.

SUMMARY OF THE INVENTION

An object of the present invention is to provide a drug having potent tissue function improving effects, particularly cerebral function improving effects and excellent safety for long-term administration.

As a result of extensive investigations, the present inventors have synthesized a great number of novel compounds and found a group of substances useful as a nootropic agent having potent pharmacological activities and excellent safety.

The above object of the present invention is accomplished by a compound represented by formula (I):

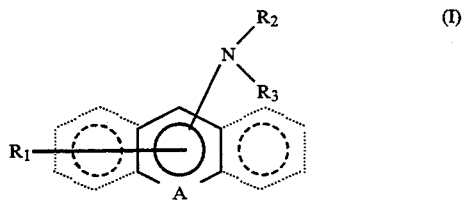

wherein A represents CH, N, or N→O (an oxidized form of pyridine or quinoline); $R_1$ represents a nitro group or an amino group; $R_2$ represents a hydrogen atom, a lower alkyl group (preferably a straight chain alkyl group of 1 to 5 carbon atoms or a branched alkyl group of 3 to 5 carbon atoms), or an acyl group (preferably an acyl group of 1 to 4 carbon atoms); and $R_3$ represents a group:

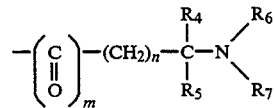

wherein m represents 0 or 1; n represents an integer of from 0 to 3; $R_4$ and $R_5$ each represents a hydrogen atom or a lower alkyl group (preferably a straight chain alkyl group of 1 to 3 carbon atoms); $R_6$ and $R_7$ each represents a hydrogen atom or a straight chain (preferably 1 to 5 carbon atoms) or branched lower alkyl group (preferably 3 to 5 carbon atoms); $R_4$ and $R_6$ may be joined together to form an alkylene chain forming a heterocyclic ring; $R_5$ and $R_7$ may be joined together to form an alkylene chain forming a heterocyclic ring; and $R_6$ and $R_7$ may be joined together to form an alkylene chain forming a heterocyclic ring, or a pharmaceutically acceptable salt thereof.

The compound of formula (I) or a pharmaceutically acceptable salt thereof exhibits excellent antidementic activities.

DETAILED DESCRIPTION OF THE INVENTION

In formula (I), the broken lines indicate that the ring need not be present. Thus, the aromatic ring skeleton includes a benzene ring, a pyridine ring, a naphthalene ring, a quinoline ring, and an anthracene ring. The term "lower alkyl group" includes a methyl group, an ethyl group, a propyl group, a butyl group, and a pentyl group. The term "branched lower alkyl group" includes an isopropyl group, an isobutyl group, a sec-butyl group, a t-butyl group, an isopentyl group, and a neopentyl group. The term "acyl group" includes a formyl group, an acetyl group, a propionyl group, and a butyryl group. The heterocyclic ring formed by a combination of $R_4$ and $R_6$ or a combination of $R_5$ and $R_7$ includes preferably a 1-azabicyclo[3.3.0]octane ring which may be substituted with a straight chain alkyl group of 1 to 3 carbon atoms (e.g., a methyl group, an ethyl group, etc.). The heterocyclic ring formed by a combination of $R_6$ and $R_7$ includes preferably a heterocyclic ring having 3 to 5 carbon atoms (e.g., a pyrrolidine ring, a piperidine ring, etc.).

The pharmaceutically acceptable salt of the compound represented by formula (I) includes inorganic acid salts (e.g., salts formed with inorganic acids such as phosphoric acid, hydrochloric acid, sulfuric acid, hydrobromic acid and hydroiodic acid), organic acid salts (e.g., salts formed with organic acids such as acetic acid, succinic acid, fumaric acid, lactic acid, tartaric acid, citric acid and methanesulfonic acid), and amino acid salts (e.g., salts formed with amino acids such as aspartic acid, glutamic acid and lysine).

The compound represented by formula (I) and pharmaceutically acceptable salts thereof are novel compounds. The compound of formula (I) or a salt thereof can be synthesized, for example, through Routes 1, 2 or 3 described below.

ROUTE 1

Route 1 comprises reacting a compound represented by formula (II):

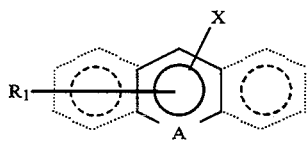

wherein A and $R_1$ are as defined above; and X represents a halogen atom or an alkoxy group,
with a compound represented by formula (III):

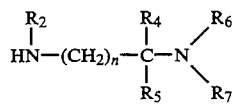

wherein n, $R_2$, $R_4$, $R_5$, $R_6$, and $R_7$ are as defined above,
and, if desired, converting the resulting compound to its salt, in order to form a compound of the following formula (I') or a pharmaceutically acceptable salt thereof:

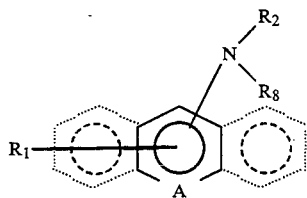

wherein A, $R_1$ and $R_2$ are as defined above: and $R_8$ represents a group:

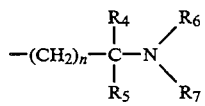

wherein n, $R_4$, $R_5$, $R_6$ and $R_7$ are as defined above.

Compound (II) and compound (III) are usually used at a molar ratio of from about 1:0.8 to about 1:5.0. The reaction is carried out with or without a solvent at a temperature of from about 0° C. to about 180° C. Solvents, which may be used, include alcohols, e.g., methanol, ethanol, and isopropanol; aromatic hydrocarbons, e.g., benzene, toluene, xylene, nitrobenzene, chlorobenzene, and dichlorobenzene; aprotic polar solvents, e.g., N,N-dimethylformamide, N,N-dimethylacetamide, and dimethyl sulfoxide; chlorinated hydrocarbons e.g., methylene chloride and chloroform; basic solvents, e.g., pyridine and triethylamine; and ethers, e.g., diethyl ether and tetrahydrofuran. If desired, the reaction may be carried out in the presence of a catalyst, such as sodium iodide or sodium bromide.

Separation and purification of the desired compound can be performed by well-known means, such as filtration, concentration, extraction, column chromatography, distillation, and recrystallization.

ROUTE 2

Route 2 comprises reducing a compound represented by formula (IV):

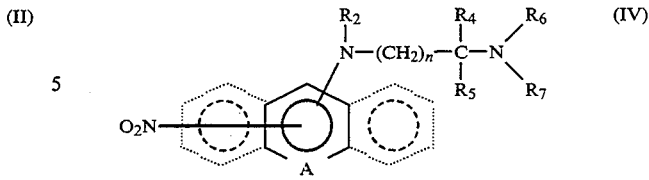

wherein A, $R_2$, n, $R_4$, $R_5$, $R_6$, and $R_7$ are as defined above, in the presence of a catalyst
and, if desired, converting the resulting compound to its salt, in order to form a compound of the following formula (I") or a pharmaceutically acceptable salt thereof:

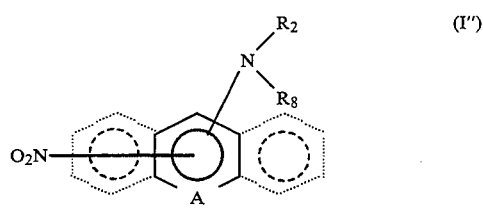

wherein A and $R_2$ are as defined above; and $R_8$ represents a group:

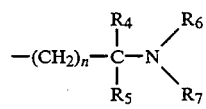

wherein n, $R_4$, $R_5$, $R_6$ and $R_7$ are as defined above.

The nitro group of the compound of formula (IV) is reduced, and the reaction is carried out in a solvent, such as methanol, ethanol, or water, in the presence of a catalyst, such as platinum or an oxide thereof, palladium or an oxide thereof, a mixture of such a platinum or palladium catalyst and a carrier (e.g., activated carbon or barium sulfate), and Raney nickel, in a hydrogen atmosphere of from 1 to 5 atm. at a temperature of from 0° C. to 100° C.

The N-oxide of the compound of formula (IV) is reduced by reacting compound (IV) with, for example, phosphorus trichloride or triphenylphosphine, in the presence or absence of a solvent, such as acetic acid, ethyl acetate, diethyl ether, benzene, or chloroform, at a temperature of from −20° to 180° C.

The reaction mixture is separated and purified in the same manner as in Route 1.

ROUTE 3

Route 3 comprises reacting a compound of formula (V):

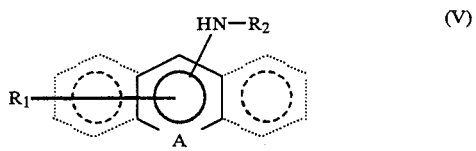

wherein A, $R_1$, and $R_2$ are as defined above,
with a compound represented by formula (VI):

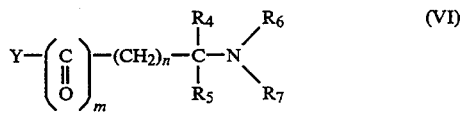

wherein m, n, R$_4$, R$_5$, R$_6$, and R$_7$ are as defined above; and Y represents a halogen atom, a hydroxyl group, or an alkoxy group, and, if desired, converting the resulting compound to its salt, in order to form a compound of formula (I) or a pharmaceutically acceptable salt thereof.

Compounds (V) and (VI) are used at a molar ratio of from about 1:0.8 to about 1:3.0. The reaction is carried out in the presence or absence of a solvent at a temperature of from −60° to 180° C. Suitable solvents include aromatic hydrocarbons, e.g., benzene, toluene, xylene, nitrobenzene, chlorobenzene, and dichlorobenzene; aprotic polar solvents, e.g., N,N-dimethylformamide, N,N-dimethylacetamide, and dimethyl sulfoxide; chlorinated hydrocarbons, e.g., methylene chloride and chloroform; basic solvents, e.g., pyridine and triethylamine; and ethers, e.g., diethyl ether and tetrahydrofuran. If desired, the reaction may be conducted in the presence of an inorganic base, e.g., NaOH, Na$_2$CO$_3$ and K$_2$CO$_3$, or an organic base, e.g., 1,8-diazabicyclo[5.4.0]-7-undecene (DBU). The reaction mixture is separated and purified in the same manner as in Route 1.

Examples of the diseases accompanied by a decline in brain function relating to the present invention include Alzheimer's disease, dementia, memory retention defect, aphasia, apraxia, psychosis, and cerebral disorders caused by cerebral infarct and cerebrosclerosis.

The compound of the present invention or a pharmaceutically acceptable salt thereof can be formulated into various preparations containing it as an active ingredient. The dose form of the preparation is not limited and include solid preparations, such as tablets, pills, hard capsules, soft capsules, powders, particles, granules, and suppositories; and liquid preparations, such as solutions, suspensions, and emulsions.

The dosage of the compound or a salt thereof depends on the kind thereof, the dose form, the degree of the disease, and the age and condition of the patient but usually range from 0.001 to 1000 mg, and preferably from 0.01 to 100 mg, per day for an adult.

The following are the examples of the formulations and these are purely illustrative and in no way to be interpreted as restrictive.

FORMULATION EXAMPLE 1

Tablet

A typical tablet prepared in a conventional manner contains the following ingredients:

| | |
|---|---|
| Compound of Example 11 | 5 mg |
| Potato starch | 55 mg |
| Microcrystalline cellulose | 30 mg |
| Gelatin | 8 mg |
| Magnesium stearate | 2 mg |
| | 100 mg |

FORMULATION EXAMPLE 2

Capsule

A typical capsule prepared using a hard gelatin capsule in a conventional manner contains the following ingredients:

| | |
|---|---|
| Compound of Example 11 | 5 mg |
| Corn starch | 106 mg |
| Lactose | 35 mg |
| Polyvinyl pyrrolidone | 2 mg |
| Magnesium stearate | 2 mg |
| | 105 mg |

The present invention is now illustrated in greater detail with reference to Examples and Test Examples, but it should be understood that the present invention is not to be construed as being limited thereto. All the percentages are by weight unless otherwise indicated.

EXAMPLE 1

4-(1-Azabicyclo[3.3.0]octan-5-yl)methylamino-3-nitroquinoline

In 60.0 ml of dimethylformamide (DMF) was dissolved 7.90 g (36.8 mmol) of 4-chloro-3-nitroquinoline, and 5.66 g (40.5 mmol) of (1-azabicyclo[3.3.0]octan-5-yl)methylamine was added to the solution under cooling with ice. After stirring at 15 to 20° C. for 20 hours, the reaction mixture was poured into 400 ml of icewater and rendered basic with sodium carbonate. The thus formed precipitate was collected by filtration, washed with water, and dried in a desiccator under reduced pressure to obtain 10.6 g (yield: 92.2%) of the titled compound as a yellow powder.

Melting point: 155°–158° C.

MS Spectrum m/z: CI/DI (i-Bu); 313 (M+1)$^+$ $^1$H-NMR Spectrum (DMSO-d$_6$) δ: 1.5–1.9 (8H, m), 2.6–2.7 (2H, m), 3.0–3.1 (2H, m), 3.81 (2H, s), 7.55 (1H, t, J=7Hz), 7.8–8.0 (2H, m), 8.47 (1H, d, J=7Hz), 9.15 (1H, brs).

EXAMPLE 2

3-Amino-4-(1-azabicyclo[3.3.0]octan-5-yl)methylaminoquinoline Hydrochloride

To 1,200 ml of ethanol were added 6.00 g (19.2 mmol) of 4-(1-azabicyclo[3.3.0]octan-5-yl)methylamino-3-nitroquinoline and 2.00 g of 10% palladium-on-carbon, and the mixture was stirred in a hydrogen stream at 15° to 20° C. for 2 hours. The reaction mixture was filtered and concentrated under reduced pressure to obtain 5.40 g (quantitative) of the titled compound as a red oil.

The resulting oil was dissolved in 200 ml of ethanol. Hydrogen chloride gas was introduced into the solution, followed by concentration. Diethyl ether was added to the concentrate, and the mixture was allowed to stand to obtain 4.80 g of the titled compound (dihydrochloride) as a pale red powder crystal.

Melting point: 231°–235° C.

MS Spectrum m/z: EI/DI; 282 (M$^+$), 110 (M-172)$^+$ $^1$H-NMR Spectrum (DMSO-d$_6$) δ: 1.7–2.2 (8H, m), 3.1–3.3 (2H, m), 3.4–3.6 (2H, m), 4.47 (2H, s), 7.75 (1H, t, J=7Hz), 7.88 (1H, t, J=7Hz), 8.10 (1H, d, J=7Hz), 8.50 (1H, brs), 8.57 (1H, s), 8.86 (1H, d, J=8Hz), 11.90 (1H, brs).

EXAMPLE 3

4-Amino-3-(1-azabicyclo[3.3.0]octan-5-yl)carbonylaminoquinoline

In 330 ml of pyridine was dissolved 5.52 g (34.7 mmol) of 3,4-diaminoquinoline. To the solution was slowly added 7.70 g (36.5 mmol) of 5-chlorocarbonyl-1-azabicyclo[3.3.0]octane hydrochloride while stirring at −15° to 20° C., followed by stirring at 15 to 20° C. for 16 hours. The reaction mixture was concentrated under reduced pressure, and 100 ml of a saturated sodium hydrogen-carbonate aqueous solution was added to the residue. The mixture was extracted with 800 ml of chloroform. The extract was washed with 40.0 ml of a sodium chloride aqueous solution, dried over sodium sulfate, and concentrated under reduced pressure. The residue was purified by alumina column chromatography to obtain 4.30 g (yield: 41.8%) of the titled compound as an oil. The resulting oil was crystallized from ethanol-diethyl ether to obtain 3.05 g of the titled compound as a pale yellow prism.

Melting point: 182°–184° C.

MS Spectrum m/z: EI/DI; 296 (M+), 110 (M-186)+

$^1$H-NMR Spectrum (DMSO-$d_6$) δ: 1.7–2.3 (5H, m), 2.6–2.8 (2H, m), 3.2–3.4 (2H, m), 6.26 (2H, s), 7.52 (1H, t, J=7Hz), 7.68 (1H, t, J=7Hz), 7.88 (1H, d, J=7Hz), 8.32 (1H, d, J=7Hz), 8.40 (1H, s), 9.83 (1H, s).

EXAMPLE 4

4-Amino-3-(1-azabicyclo[3.3.0]octan-5-yl)methylcarbonylaminoquinoline 3,4-Diaminoquinoline and 5-chlorocarbonylmethyl-1-azabicyclo[3.3.0]octane hydrochloride were reacted in the same manner as in Example 3 to obtain the titled compound in a yield of 53.0%.

Melting point: 205°–209° C.

MS Spectrum m/z: EI/DI; 310 (M+), 110 (M-200)$^{30}$ $^1$H-NMR Spectrum (DMSO-$d_6$) δ: 1.6–2.1 (8H, m), 2.41 (2H, s), 2.5–2.7 (2H, m), 2.9–3.1 (2H, m), 6.78 (2H, s), 7.42 (1H, t, J=8Hz), 7.59 (1H, t, J=8Hz), 7.77 (1H, d, J=8Hz), 8.18 (1H, d, J=8Hz), 8.24 (1H, s), 9.35 (1H, s).

EXAMPLE 5

3-(1-Azabicyclo[3.3.0]octan-5-yl)-methylamino-4-nitroquinoline 1-oxide

3-Bromo-4-nitroquinoline N-oxide and (1-azabicyclo[3.3.0]octan-5-yl)methylamine were reacted in the same manner as in Example 1 to obtain the titled compound in a yield of 88.4%.

Melting point: 90°–92° C.

MS Spectrum m/z: CI/DI (i-Bu); 346 (M+18)+, 266 (M-62)+

$^1$H-NMR Spectrum (CDCl$_3$) δ: 1.6–2.0 (8H, m), 2.6–2.8 (2H, m), 3.1–3.3 (2H, m), 3.48 (2H, d, J=4Hz), 5.91 (1H, brs), 7.57 (1H, t, J=8Hz), 7.75 (1H, t, J=1Hz), 8.12 (1H, d, J=8Hz), 8.56 (1H, s), 8.73 (1H, d, J=8Hz).

EXAMPLE 6

3-(1-Azabicyclo[3.3.0]octan-5-yl)methylamino-4-nitroquinoline

In 60.0 ml of chloroform was dissolved 900 mg (2.74 mmol) of 3-(1-azabicyclo[3.3.0]octan-5-yl)-methylamino-4-nitroquinoline-1-oxide, and 4.76 ml (47.4 mmol) of phosphorus trichloride was added thereto dropwise while cooling at −10° C. After the addition, the mixture was stirred at 0° C. for 16 hours. The reaction mixture was poured into 500 ml of ice-water, made basic with sodium hydrogencarbonate, and extracted with chloroform. The extract was dried over sodium sulfate, concentrated under reduced pressure, purified by alumina column chromatography, and crystallized from chloroformhexane to obtain 560 mg (yield: 65.4%) of the titled compound as a pale yellow powder crystal.

Melting point: 95°–99° C.

MS Spectrum m/z: CI/DI (i-Bu); 348 (M+36)+, 266 (M-46)+

$^1$H-NMR Spectrum (CDCl$_3$) δ: 1.6–2.0 (8H, m), 2.6–2.8 (2H, m), 3.1–3.3 (2H, m), 3.60 (2H, d, J=4Hz), 6.01 (1H, brs), 7.40 (1H, t, J=8Hz), 7.61 (1H, t, J=8Hz), 7.95 (1H, d, J=8Hz), 8.09 (1H, d, J=8Hz), 8.63 (1H, s).

EXAMPLE 7

3-[2-(1-Azabicyclo[3.3.0]octan-5-yl)-ethyl]amino-4-nitroquinoline 1-oxide

3-Bromo-4-nitroquinoline 1-oxide and 2-(1-azabicyclo[3.3.0]octan-5-yl)ethylamine were reacted in the same manner as in Example 1 to obtain the titled compound in a yield of 87.4%.

Melting point: 103°–106° C.

MS Spectrum m/z: CI/DI (i-Bu); 360 (M+20)+, 280 (M-62)+

$^1$H-NMR Spectrum (CDCl$_3$) δ: 1.6–1.9 (10H, m), 2.6–2.8 (2H, m), 3.0–3.2 (2H, m), 3.90 (2H, dd, J=11, 7Hz), 7.53 (1H, t, J=8Hz), 7.72 (1H, t, J=8Hz), 8.10 (1H, d, J=8Hz), 8.50 (1H, brs), 8.53 (1H, s), 8.73 (1H, d, J=8Hz).

EXAMPLE 8

3-[2-(1-Azabicyclo[3.3.0]octan-5-yl)ethyl]amino-4-nitroquinoline

3-[2-(1-Azabicyclo[3.3.0]octan-5-yl)ethyl]amino-4-nitroquinoline 1-oxide and phosphorus trichloride were reacted in the same manner as in Example 6 to obtain the titled compound in a yield of 66.3%.

Melting point: 106°–108° C.

MS Spectrum m/z: CI/DI (i-Bu); 362 (M+36)+, 280 (M-46)+

$^1$H-NMR Spectrum (CDCl$_3$) δ: 1.5–2.0 (10H, m), 2.6–2.8 (2H, m), 3.0–3.2 (2H, m), 3.96 (2H, dd, J=10, 6Hz), 7.38 (1H, t, J=8Hz), 7.59 (1H, t, J=8Hz), 7.92 (1H, d, J=8Hz), 8.07 (1H, d, J=8Hz), 8.17 (1H, brs), 8.58 (1H, s).

EXAMPLE 9

1-(1-Azabicyclo[3.3.0]octan-5-yl)methylamino-2-nitrobenzene o-Chloronitrobenzene and 1-azabicyclo[3.3.0]octan-5-yl)methylamine were reacted in the same manner as in Example 1 to obtain the titled compound as an oil in a yield of 80.9%.

MS Spectrum m/z: EI/DI; 261 (M+), 110 (M-151)+

$^1$H-NMR Spectrum (CDCl$_3$) δ: 1.6–1.9 (5H, m), 2.6–2.7 (2H, m), 3.1–3.2 (2H, m), 3.16 (2H, d, J=5Hz), 6.60 (1H, t, J=9Hz), 6.83 (1H, d, J=9Hz), 7.40 (1H, t, J=9Hz), 8.16 (1H, d, J=9Hz), 8.36 (1H, brs).

EXAMPLE 10

1-(1-Azabicyclo[3.3.0]octan-5-yl)methylamino-4-nitrobenzene p-Chloronitrobenzene and (1-azabicyclo[3.3.0]octan-5-yl)methylamine were reacted in the same manner as in Example 1 to obtain the titled compound as an oil in a yield of 74.4 %.

MS Spectrum m/z: EI/DI; 261 (M+), 110 (M-151)+
¹H-NMR Spectrum (CDCl₃) δ: 1.6–1.9 (5H, m), 2.6–2.7 (2H, m), 2.9–3.1 (2H, m), 3.04 (2H, d, J=5Hz), 5.27 (1H, brs), 6.53 (2H, d, J=9Hz), 8.06 (2H, d, J=9Hz).

EXAMPLE 11

1-(1-Azabicyclo[3.3.0]octan-5-yl)methylamino-4-nitronaphthalene

1-Chloro-4-nitronaphthalene and (1-azabicyclo[3.3.0]octan-5-yl)methylamine were reacted in the same manner as in Example 1 to obtain the titled compound in a yield of 50.9%.

Melting point: 143°–144° C.

MS Spectrum m/z: EI/DI; 311 (M+), 110 (M-201)+ m/z: CI/DI (i-Bu); 312 (M+1)+, 110 (M-201)+

¹H-NMR Spectrum (CDCl₃) δ: 1.7–2.0 (8H, m), 2.7–2.8 (2H, m), 3.1–3.2 (2H, m), 3.19 (2H, d, J=4Hz), 6.45 (1H, d, J=9Hz), 6.50 (1H, brs), 7.53 (1H, t, J=8Hz), 7.70 (1H, t, J=8Hz), 7.88 (1H, d, J=8Hz), 8.49 (1H, d, J=9Hz), 9.07 (1H, d, J=8Hz).

EXAMPLE 12

2-(1-Azabicyclo[3.3.0]octan-5-yl)methylamino-1-nitronaphthalene

2-Ethoxy-1-nitronaphthalene and (1-azabicyclo[3.3.0]octan-5-yl)methylamine were reacted in the same manner as in Example 1 to obtain the titled compound in a yield of 39.1%.

Melting point: 86°–87° C.

MS Spectrum m/z: EI/DI; 311 (M+), 110 (M-201)+ m/z: CI/DI (i-Bu); 312 (M+1)+, 110 (M-201)+

¹H-NMR Spectrum (CDCl₃) δ: 1.6–1.9 (8H, m), 2.6–2.7 (2H, m), 3.1–3.2 (2H, m), 3.30 (2H, d, J=5Hz), 7.06 (1H, d, J=9Hz), 7.31 (1H, d, J=8Hz), 7.58 (1H, d, J=8Hz), 7.65 (1H, d, J=8Hz), 7.76 (1H, d, J=9Hz), 8.77 (1H, d, J=8Hz), 9.18 (1H, brs)

EXAMPLE 13

1-(1-Azabicyclo[3.3.0]octan-5-yl)methylamino-2-nitronaphthalene

1-Chloro-2-nitronaphthalene and (1-azabicyclo[3.3.0]octan-5-yl)methylamine were reacted in the same manner as in Example 1 to obtain the titled compound in a yield of 84.1%.

Melting point: 88°–89° C.

MS Spectrum m/z: EI/DI; 311 (M+), 110 (M-201)+

¹H-NMR Spectrum (CDCl₃) δ: 1.6–1.9 (8H, m), 2.6–2.7 (2H, m), 3.1–3.2 (2H, m), 3.69 (2H, d, J=5Hz), 7.05 (1H, d, J=9Hz), 7.43 (1H, t, J=8Hz), 7.59 (1H, t, J=8Hz), 7.73 (1H, d, J=8Hz), 8.08 (1H, d, J=9Hz), 8.31 (1H, d, J=8Hz), 9.49 (1H, brs).

EXAMPLE 14

1-(2-Diisopropylaminoethyl)amino-4-nitronaphthalene

1-Chloro-4-nitronaphthalene and N,N-diisopropylethylenediamine were reacted in the same manner as in Example 1 to obtain the titled compound in a yield of 75.7%.

Melting point: 63°–64° C.

MS Spectrum m/z: EI/DI; 315 114 (M-201)+

¹H-NMR Spectrum (CDCl₃) δ: 1.10 (12H, d, J=7Hz), 2.93 (2H, t, J=6Hz), 3.13 (2H, 7tet, 7Hz), 3.28 (2H, q, J=6Hz), 6.43 (1H, d, J=9Hz), 6.60 (1H, brs), 7.51 (1H, t, J=8Hz), 7.70 (1H, t, J=8Hz), 7.81 (1H, d, J=8Hz), 8.50 (1H, d, J=9Hz), 9.07 (1H, d, J=8Hz).

EXAMPLE 15

1[N-(1-Azabicyclo[3.3.0]octan-5-yl)methyl-N-methylamino]-4-nitronaphthalene

1-Chloro-4-nitronaphthalene and 5-(methylamino)methyl-1-azabicyclo[3.3.0]octane were reacted in the same manner as in Example 1 to obtain the titled compound as an oil in a yield of 78.2%.

MS Spectrum m/z: CI/DI (i-Bu); 326 (M+1)+, 110 (M-215)+

¹H-NMR Spectrum (CDCl₃) δ: 1.5–2.0 (8H, m), 2.5–2.6 (2H, m), 2.9–3.0 (2H, m), 3.12 (3H, s), 3.37 (2H, s), 7.11 (1H, d, J=8Hz), 7.55 (1H, t, J=8Hz), 7.68 (1H, t, J=8Hz), 8.26 (1H, d, J=8Hz), 8.31 (1H, d, J=8Hz), 8.78 (1H, d, J=8Hz).

EXAMPLE 16

1-[2-(1-Azabicyclo[3.3.0]octan-5-yl)ethylamino]-4-nitronaphthalene

1-Chloro-4-nitronaphthalene and 2-(1-azabicyclo-3.3.0]octan-5-yl)ethylamine were reacted in the same manner as in Example 1 to obtain the titled compound in a yield of 65.6%.

Melting point: 90°–91° C.

MS Spectrum m/z: EI/DI; 325 (M+), 110 (M-215)+

¹H-NMR Spectrum (CDCl₃) δ: 1.6–1.9 (8H, m), 1.94 (2H, t, J=6Hz), 2.7–2.8 (2H, m), 3.1–3.2 (2H, m), 3.48 (2H, t, J=6Hz), 6.34 (1H, d, J=9Hz), 7.49 (1H, t, J=8Hz), 7.68 (1H, t, J=8Hz), 7.84 (1H, d, J=8Hz), 8.54 (1H, d, J=9Hz), 9.11 (1H, d, J=9Hz), 9.80 (1H, brs).

EXAMPLE 17

1-(1-Azabicyclo[3.3.0]octan-5-yl)methylamino-5-nitronaphthalene

1-Amino-5-nitronaphthalene and 5-chloromethyl-1-azabicyclo[3.3.0]octane were reacted in the same manner as in Example 3 to obtain the titled compound in a yield of 45.3%.

Melting point: 95°–97° C.

MS Spectrum m/z: CI/DI (i-Bu); 312 (M+1)+, 110 (M-201)+

¹H-NMR Spectrum (CDCl₃) δ: 1.7–2.0 (8H, m), 2.7–2.8 (2H, m), 3.06 (2H, d, J=5Hz), 3.1–3.2 (2H, m), 5.39 (1H, brs, g), 6.67 (1H, d, J=8Hz), 7.45 (1H, t, J=8Hz), 7.52 (1H, t, J=8Hz), 7.76 (1H, d, J=8Hz), 8.11 (1H, d, J=8Hz), 8.16 (1H, d, J=8Hz).

EXAMPLE 18

1-[N-(1-Azabicyclo[3.3.0]octan-5-yl)methyl-N-methylamino]-2-nitronaphthalene

1-Chloro-2-nitronaphthalene and 5-(methylamino)methyl-1-azabicyclo[3.3.0]octane were reacted in the same manner as in Example 1 to obtain the titled compound as an oil in a yield of 85.9%.

MS Spectrum m/z: CI/DI (i-Bu); 326 (M+1)+, 110 (M-215)+

¹H-NMR Spectrum (CDCl₃) δ: 1.4–1.8 (8H, m), 2.5–2.6 (2H, m), 2.9–3.0 (2H, m), 2.97 (2H, s), 3.23 (2H, s), 7.6–7.7 (2H, m), 7.62 (1H, d, J=9Hz), 7.69 (1H, d, J=9Hz), 7.8–7.9 (1H, m), 8.3–8.4 (1H, m).

EXAMPLE 19

9-(1-Azabicyclo[3.3.0]octan-5-yl)methylamino-10-nitroanthracene

9-Bromo-10-nitroanthracene and (1-azabicyclo[3.3.0]octan-5-yl)methylamine were reacted in the same manner as in Example 1 to obtain the titled compound in a yield of 51.5%.

Melting point: 114°–116° C.

MS Spectrum m/z: EI/DI; 361 (M+), 110 (M-251)+

1H-NMR Spectrum (CDCl3) δ: 1.6–1.9 (8H, m), 2.7–2.8 (2H, m), 3.2–3.3 (2H, m), 3.43 (2H, s), 7.45 (2H, t, J=9Hz), 7.70 (2H, t, J=9Hz), 8.07 (2H, d, J=9Hz), 8.54 (2H, d, J=9Hz).

TEST EXAMPLE 1

Effect on Memory Retention Defect

A passive avoidance learning test using mice was conducted to examine whether scopolamine-induced inhibition of memory retention can be improved by the compound of the present invention.

Experimental Equipment

A training box composed of a light room and a dark room having the same structure was used. The dark room is designed so that a foot shock is given to a test animal via a grid of the floor. An opening is provided on the partitioning wall of the two rooms to let animals in and out freely.

Preparation of Retention Defect Model

Scopolamine hydrobromide dissolved in physiological saline was intraperitoneally administered to a mouse at a dose of 0.25 mg/kg.

Administration of Test Compound

Five minutes after the scopolamine administration, a test compound was intraperitoneally administered to the mouse at a dose shown in Table 1 below (test group).

Training (Engram Acquirement Test)

The animal was put in the light room. Immediately after the animal moved into the dark room, a foot shock was given until the animal returned to the light room.

Remembrance Test

After 24 hours from the training, the animal was again put in the light room, and the time required for the animal's moving to the dark room was measured up to 300 seconds.

Data Analysis and Results

The data from the remembrance test were analyzed to obtain a percent prolongation of the memory retention time of the test group based on that of the control group having received no test compound. The results obtained are shown in Table 1 below.

TABLE 1

| Test Compound | Dose (μg/kg) | Number of Animals per Group | Percent Prolongation (%) |
|---|---|---|---|
| Example 6 | 1000 | 20 | 55.1 |
| Example 10 | 1000 | 20 | 26.5 |
| Example 11 | 1 | 20 | 30.9 |
| " | 10 | 20 | 91.7 |
| " | 100 | 20 | 120.9 |
| " | 1000 | 20 | 152.6 |
| Example 15 | 0.01 | 20 | 111.6 |
| " | 0.1 | 20 | 68.8 |
| " | 1 | 20 | 85.2 |
| Example 18 | 0.01 | 20 | 117.9 |
| " | 0.1 | 20 | 115.9 |
| THA | 100 | 20 | 24.4 |
| " | 1000 | 20 | 74.8 |

TEST EXAMPLE 2

Inhibitory Effect on 3H-Pirenzepine Bonding to Rat Brain Homogenate

Preparation of Rat Brain Homogenate

A rat brain homogenate was prepared according to the method of Yamamura and Synder (Proc. Nat. Acad. Sci. USA, Vol. 71, pp. 1725–1729 (1974)).

An SD male rat was sacrificed by decapitation, and the brain excised. After the cerebellum was removed, 0.32 M sucrose was added thereto in an amount 10 times the weight of the brain under ice cooling, followed by homogenizing in a Potter-Elvehjem glass homogenizer. The resulting homogenate was centrifuged at 1000×g for 10 minutes, the precipitate removed, and the supernatant further homogenized with a Polytron (manufactured by KINEMATICA) to obtain a rat brain homogenate for testing.

3H-Pirenzepine Bonding Inhibition Test

The method of Flynn and Mash (J. Pharm. Exp. Therm., Vol. 250, pp. 573–581 (1989)) was followed.

A mixture consisting of 0.035 ml of the above prepared rat brain homogenate (protein content: 0.6 mg), 1 ml of a 50 mM phosphoric acid buffer (pH 7.4) containing 2.0 nM 3H-pirenzepine, and 1 ml of a test compound dissolved in the same buffer was allowed to react at room temperature for 60 minutes. To the reaction mixture was added 3.0 ml of the same buffer as used above as cooled with ice, and the mixture was filtered through Whatman GF/B filter paper having been previously impregnated with a 0.1% polyethyleneimine solution for 60 minutes. The filter cake was washed twice with 3.0 ml of the same buffer, the filter paper taken out, an emulsion scintillator added, and the scintillation measured with a liquid scintillation counter to obtain a 50% inhibitory concentration (IC50) of the test compound on 3H-pirenzepine bonding to the rat brain homogenate. The results obtained are shown in Table 2 below.

TABLE 2

| Test Compound | IC$_{50}$ (μM) |
|---|---|
| Example 6 | 1.2 |
| Example 11 | 0.9 |
| Example 14 | 0.9 |
| Example 15 | 0.04 |
| Example 17 | 0.8 |
| Example 18 | 0.44 |
| Example 19 | 1.4 |

TEST EXAMPLE 3

Acute Toxicity Test

The compound of Example 11, suspended in 5% gum arabic, was intraperitoneally achninistered to a 5-week-old day male mouse. General manifestation of toxicity was observed over 60 minutes after the administration, and the animal's death was observed up to 24 hours from the administration. As a result, neither general manifestation of toxicity nor death was observed at a dose of 100 mg/kg.

As described and demonstrated above, the present invention provides a novel compound useful as a nootropic agent and particularly as a preventive and treating agent of cerebral dysfunction and a process for preparing the same. The compound of the present invention provides a high degree of safety for long-term administration, and therefore is an effective treating agent of dementia, memory retention defect, aphasia, psychosis, and Alzheimer's disease as well as cerebral infarct and cerebrosclerosis.

While the invention has been described in detail and with reference to specific examples thereof, it will be apparent to one skilled in the art that various changes and modifications can be made therein without departing from the spirit and scope thereof.

What is claimed is:

1. A compound represented by formula (I):

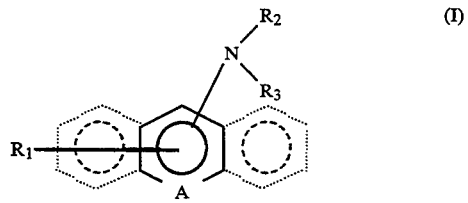

wherein A represents CH, N, or N→O; $R_1$ represents a nitro group or an amino group; $R_2$ represents a hydrogen atom, or a lower alkyl group; and $R_3$ represents:

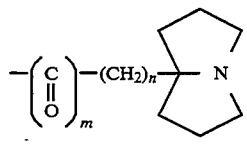

wherein m represents 0 or 1; and
n represents an integer of from 0 to 3, or a pharmaceutically acceptable salt thereof.

2. The compound as claimed in claim 1, wherein said compound is selected from the group consisting of 4-(1-azabicyclo[3.3.0]octan-5-yl)methylamino-3-nitroquinoline, 3-amino-4-(1-azabicyclo[3.3.0]octan-5-yl)methylaminoquinoline, 4-amino-3-(1-azabicyclo[3.3.0]octan-5-yl)carbonylaminoquinoline, 4-amino-3-(1-azabicyclo[3.3.0]octan-5-yl)-methylcarbonylaminoquinoline, 3-(1-azabicyclo[3.3.0]octan-5-yl)methylamino-4-nitroquinoline 1-oxide, 3-(1-azabicyclo[3.3.0]octan-5-yl)methylamino-4-nitroquinoline, 3-[2-(1-azabicyclo[3.3.0]octan-5-yl)ethyl]amino-4-nitroquinoline 1-oxide, 3-[2-(1-azabicyclo[3.3.0]octan-5-yl(ethyl]amino-4-nitroquinoline, 1-(1-azabicyclo[3.3.0]octan-5-yl)methylamino-2-nitrobenzene, 1-(1-azabicyclo[3.3.0]octan-5-yl)methylamino-4-nitrobenzene, 1-(1-azabicyclo[3.3.0]octan-5-yl)methylamino-4-nitronaphthalene, 2-(1-azabicyclo[3.3.0]octan-5-yl)methylamino-1-nitronaphthalene, 1-(1-azabicyclo[3.3.0]octan-5-yl)methylamino-2-nitronaphthalene, 1-[N-(1-azabicyclo[3.3.0]octan-5-yl)methyl-N-methylamino]-4-nitronaphthalene, 1-[2-(1-azabicyclo[3.3.0]octan-5-yl)ethylamino]-4-nitronaphthalene, 1-(1-azabicyclo[3.3.0]octan-5-yl)methylamino-5-nitronaphthalene, 1-[N-(1-azabicyclo[3.3.0]octan-5-yl)methyl-N-methylamino]-2-nitronaphthalene, and 9-(1-azabicyclo[3.3.0]octan-5-yl)methylamino-10-nitroanthracene.

3. A pharmaceutical composition, comprising at least one compound represented by formula (I):

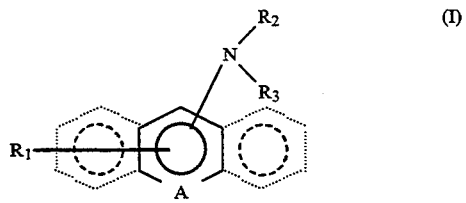

wherein A represents CH, N, or N→O; $R_1$ represents a nitro group or an amino group; $R_2$ represents a hydrogen atom, or a lower alkyl group; and $R_3$ represents:

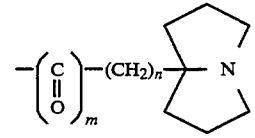

wherein m represents 0 or 1; and
n represents an integer of from 0 to 3, or a pharmaceutically acceptable salt thereof as an active ingredient, together with a pharmaceutically acceptable carrier.

4. A method of preventing or treating a brain dysfunction, comprising administering to a human in need thereof a brain dysfunction preventing or treating effective amount of a compound represented by the following formula (I):

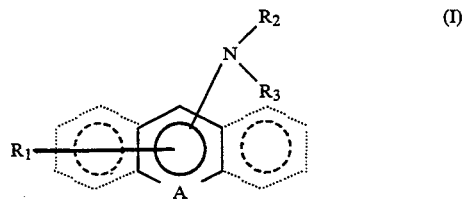

wherein A represents CH, N, or N→O; $R_1$ represents a nitro group or an amino group; $R_2$ represents a hydrogen atom, or a lower alkyl group; and $R_3$ represents:

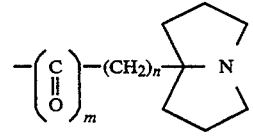

wherein m represents 0 or 1; and
n represents an integer of from 0 to 3, or a pharmaceutically acceptable salt thereof, together with a pharmaceutically acceptable carrier.

5. The method as claimed in claim 4, wherein said dysfunction is Alzheimer's disease, dementia, memory retention defect, aphasia, apraxia, psychosis, or cerebral disorders caused by cerebral infarct and cerebrosclerosis.

6. The compound as claimed in claim 1, wherein the lower alkyl group of $R_2$ is a straight chain alkyl group having 1 to 5 carbon atoms or a branched alkyl group having 3 to 5 carbon atoms.

7. The pharmaceutical composition as claimed in claim 3, wherein said compound is selected from the group consisting of 4-(1-azabicyclo[3.3.0]octan-5-yl)methylamino-3-nitroquinoline, 3-amino-4-(1-azabicyclo[3.3.0]octan-5-yl)methylaminoquinoline, 4-amino-3-(1-azabicyclo[3.3.0]octan-5-yl)carbonylaminoquinoline, 4-amino-3-(1-azabicyclo[3.3.0]octan-5-yl)methylcarbonylaminoquinoline, 3-(1-azabicyclo[3.3.0]octan-5-yl)methylamino-4-nitroquinoline 1 oxide, 3-(1azabicyclo[3.3.0]octan-5-yl)methylamino-4-nitroquinoline, 3-[2-(1-azabicyclo[3.3.0]octan-5-yl)ethyl]amino-4-nitroquinoline 1 oxide, 3-[2-(1-azabicyclo[3.3.0]octan-5-yl)ethyl]amino-4-nitroquinoline, 1-(1-azabicyclo[3.3.-

0]octan-5-yl)methylamino-2-nitrobenzene, 1-(1-azabicyclo[3.3.0]octan-5-yl)methylamino-4-nitrobenzene, 1-(1-azabicyclo[3.3.0]octan-5-yl)methylamino-4-nitronaphthalene, 2-(1-azabicyclo[3.3.0]octan-5-yl)methylamino-1-nitronaphthalene, 1-(1-azabicyclo[3.3.0]octan-5-yl)methylamino-2-nitronaphthalene, 1-[N-(1azabicyclo[3.3.0]octan-5-yl)methyl-N-methylamino]-4-nitronaphthalene, 1-[2-(1-azabicyclo[3.3.0]octan-5-yl)ethylamino]-4-nitronaphthalene, 1-(1-azabicyclo[3.3.0]octan-5-yl)methylamino]-5-nitronaphthalene, 1-[N-(1-azabicyclo[3.3.0]octan-5-yl)methyl-N-methylamino]-2-nitronaphthalene, and 9-(1-azabicyclo[3.3.0]octan-5-yl)methylamino-10-nitroanthracene.

8. The pharmaceutical composition as claimed in claim 3, wherein the lower alkyl group of $R_2$ is a straight chain alkyl group having 1 to 5 carbon atoms or a branched alkyl group having 3 to 5 carbon atoms.

9. A method as claimed in claim 4, wherein said compound is selected from the group consisting of 4-(1-azabicyclo[3.3.0]octan-5-yl)methylamino-3-nitroquinoline, 3-amino-4-(1-azabicyclo[3.3.0]octan-5-yl)methylaminoquinoline, 4-amino-3-(1-azabicyclo[3.3.0]octan-5-yl)carbonylaminoquinoline, 4-amino-3-(1-azabicyclo[3.3.0]octan-5-yl)methylcarbonylaminoquinoline, 3-(1-azabicyclo [3.3.0]octan-5-yl)methylamino-4-nitroquinoline 1 oxide, 3-(1-azabicyclo[3.3.0]octan-5-yl)methylamino-4-nitroquinoline, 3-[2-(1-azabicyclo[3.3.0]octan-5-yl)ethyl]amino-4-nitroquinoline1 oxide, 3-[2-(1-azabicyclo[3.3.0]octan-5-yl)ethyl]amino-4-nitroquinoline, 1-(1-azabicyclo[3.3.0]octan-5-yl)methylamino-2-nitrobenzene, 1-(1-azabicyclo[3.3.0]octan-5-yl)methylamino-4-nitrobenzene, 1-(1-azabicyclo[3.3.0]octan-5-yl)methylamino-4-nitronaphthalene, 2-(1-azabicyclo[3.3.0]octan-5-yl)methylamino-1 -nitronaphthalene, 1-(1-azabicyclo[3.3.0]octan-5-yl)methylamino-2-nitronaphthalene, 1-[N-(1-azabicyclo[3.3.0]octan-5-yl)methyl-N-methylamino]-4-nitronaphthalene1-[2 -(1-azabicyclo[3.3.0]octan-5-yl)ethylamino]-4-nitronaphthalene, 1-(1-azabicyclo[3.3.0]octan-5-yl)methylamino]-5-nitronaphthalene, 1-]N-(1-azabicyclo[3.3.0]octan-5-yl)methyl-N-methylamino]-2-nitronaphthalene, and 9-(1-azabicyclo[3.3.0]octan-5-yl)methylamino-10-nitroanthracene.

10. The method as claimed in claim 4, wherein the lower alkyl group of $R_2$ is a straight chain alkyl group having 1 to 5 carbon atoms or a branched alkyl group having 3 to 5 carbon atoms.

11. The method as claimed in claim 4, wherein brain dysfunction preventing or treating effective amount is between 0.001 to 1,000 mg per day.

12. The method as claimed in claim 11, wherein said brain dysfunctional preventing or treating effective amount is between 0.01 to 100 mg per day.

* * * * *